(12) United States Patent
LeVahn et al.

(10) Patent No.: US 7,458,933 B2
(45) Date of Patent: *Dec. 2, 2008

(54) METHOD FOR KNEE-JOINT SURGERY

(75) Inventors: Steven M. LeVahn, Lino Lakes, MN (US); Robert Ballantine, Hudson, WI (US); Todd W. Sharratt, Stillwater, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 495 days.

This patent is subject to a terminal disclaimer.

(21) Appl. No.: 10/892,816

(22) Filed: Jul. 16, 2004

(65) Prior Publication Data

US 2005/0027171 A1    Feb. 3, 2005

Related U.S. Application Data

(63) Continuation-in-part of application No. 10/728,202, filed on Dec. 4, 2003, now Pat. No. 7,264,589, and a continuation-in-part of application No. 10/623,179, filed on Jul. 18, 2003, which is a continuation of application No. 10/077,693, filed on Feb. 15, 2002, now Pat. No. 6,659,944, which is a continuation of application No. 09/990,420, filed on Nov. 21, 2001, now Pat. No. 6,368,271.

(60) Provisional application No. 60/396,850, filed on Jul. 18, 2002.

(51) Int. Cl.
*A61B 1/32* (2006.01)
*A61F 2/38* (2006.01)

(52) U.S. Cl. ............................ 600/227; 623/20.14
(58) Field of Classification Search ................. 600/184, 600/201, 226, 227, 228–235
See application file for complete search history.

(56) References Cited

U.S. PATENT DOCUMENTS

| 2,586,488 | A | * | 2/1952 | Smith | .......................... 600/233 |
| 3,522,799 | A | | 8/1970 | Gauthier | |
| 3,810,462 | A | * | 5/1974 | Szpur | .......................... 600/234 |
| 4,034,418 | A | * | 7/1977 | Jackson et al. | ............. 623/20.3 |

(Continued)

FOREIGN PATENT DOCUMENTS

DE    4103070    8/1991    .................. 606/90

(Continued)

OTHER PUBLICATIONS

Translation of German Patent DE 41 03 070A1. Inventor: Jacques Belin.*

(Continued)

*Primary Examiner*—Anu Ramana
(74) *Attorney, Agent, or Firm*—Westman, Champlin & Kelly, P.A.

(57) ABSTRACT

A method of performing knee-joint surgery includes positioning the tibia and the femur such that the knee-joint is disposed in a bent position. An incision is made to expose the knee-joint. A retractor support is mounted to a surgical table. The skin and flesh layers proximate the knee-joint are retracted utilizing a retractor that is attached to the retractor support which is mounted to a surgical table.

8 Claims, 3 Drawing Sheets

U.S. PATENT DOCUMENTS

| | | | | |
|---|---|---|---|---|
| 4,215,439 A * | 8/1980 | Gold et al. | ............... | 623/20.26 |
| 4,261,062 A | 4/1981 | Amstutz et al. | ............... | 3/1.91 |
| 4,373,709 A | 2/1983 | Whitt | ......................... | 269/328 |
| 4,380,999 A | 4/1983 | Healy | ......................... | 60/234 |
| 4,520,797 A | 6/1985 | Petersen | ..................... | 128/20 |
| 4,940,066 A | 7/1990 | Santilli et al. | ............... | 128/882 |
| 4,971,037 A * | 11/1990 | Pelta | ......................... | 600/234 |
| 5,217,463 A | 6/1993 | Mikhail | ..................... | 606/88 |
| 5,290,220 A | 3/1994 | Guhl | .......................... | 602/33 |
| 5,290,290 A | 3/1994 | Mikhail | ..................... | 606/88 |
| 5,308,349 A | 5/1994 | Mikhail | ..................... | 606/88 |
| 5,308,350 A | 5/1994 | Mikhail | ..................... | 606/88 |
| 5,334,194 A | 8/1994 | Mikhail | ..................... | 606/88 |
| 5,380,331 A | 1/1995 | Mikhail | ..................... | 606/79 |
| 5,437,677 A | 8/1995 | Shearer et al. | ................ | 606/96 |
| 5,441,042 A | 8/1995 | Putman | ..................... | 601/109 |
| 5,454,365 A | 10/1995 | Bonutti | ..................... | 600/204 |
| 5,507,817 A | 4/1996 | Craig et al. | .................... | 623/18 |
| 5,645,079 A | 7/1997 | Zahiri et al. | ................ | 128/846 |
| 5,685,826 A | 11/1997 | Bonutti | ..................... | 600/204 |
| 5,702,486 A | 12/1997 | Craig et al. | .................... | 623/23 |
| 5,707,390 A | 1/1998 | Bonutti | ..................... | 600/204 |
| 5,716,325 A | 2/1998 | Bonutti | ..................... | 600/204 |
| 5,769,783 A * | 6/1998 | Fowler | ....................... | 600/226 |
| 5,782,924 A | 7/1998 | Johnson | ..................... | 623/20 |
| 5,795,291 A | 8/1998 | Koros et al. | ................. | 600/232 |
| 5,888,196 A | 3/1999 | Bonutti | ..................... | 600/204 |
| 5,902,233 A | 5/1999 | Farley et al. | ................ | 600/213 |
| 5,954,739 A | 9/1999 | Bonutti | ..................... | 600/207 |
| 5,961,512 A | 10/1999 | Purnell | .......................... | 606/1 |
| 5,964,698 A * | 10/1999 | Fowler | ....................... | 600/217 |
| 6,030,340 A | 2/2000 | Maffei et al. | ................ | 600/233 |
| 6,090,042 A | 7/2000 | Rullo et al. | ................. | 600/210 |
| 6,102,853 A | 8/2000 | Scirica et al. | ............... | 600/227 |
| 6,315,718 B1 | 11/2001 | Sharratt | ....................... | 600/228 |
| 6,340,345 B1 | 1/2002 | Lees et al. | .................. | 600/226 |
| 2003/0199738 A1 * | 10/2003 | Yager | ......................... | 600/227 |

FOREIGN PATENT DOCUMENTS

FR 2339936 * 8/1977

OTHER PUBLICATIONS

Dandy, The Wishbook Trust, Wishbone Casebook, Total Knee Replacement, 1998, 3 pages.
Huddleston, Arthritis of the Knee Joint, Implant Designs and Materials, 1992, 2 pages.
Huddleston, Arthritis of the Knee Joint, Total Knee Replacement Surgery, 1999, 4 pages.
Huddleston, Arthritis of the Knee Joint, Other Surgery Options for Knee Arthritis, 1999, 2 pages.
Webpage, Why is Total Knee Replacement Surgery Necessary?, Medformation.com, Allina Hospitals & Clinics, 2002, 2 pages.
University of Washington School of Medicine, Diagnostic Radiology Residency Programs, Normal Knee Anatomy, 2002, 4 pages.
Webpage, 1Up Health, Knee Joint Replacement, 2003, 3 pages.
Webpage, A.D.A.M, Medical Encyclopedia, Knee Joint Replacement—series: Aftercare, 2002, 2 pages.
Webpage, A.D.A.M., Medical Encyclopedia, Knee Joint Replacement—series: Procedure, 2002, 2 pages.
Webpage, A.D.A.M., Medical Encyclopedia, Knee Joint Replacement—series: Indications, 2002, 2 pages.
Webpage, A.D.A.M., Medical Encyclopedia, Knee Joint Replacement—series: Normal Anatomy, 2002, 1 page.
Webpage, DePuy Orthopaedics, Inc., Knee Replacement Surgery using the LCS® Complete™ Mobile—Bearing Knee System, 2003, 4 pages.
Webpage, G. Hendrickson, Discovery Communications Inc., Knee Joint Replacement, Jul. 9, 2003, 2 pages.
Webpage, DePuy Orthopaedics, Inc., LCS® Complete™ Mobile Bearing Knee System More Natural Movement from Knee Replacement Surgery, 2003, 4 pages.
Webpage, J.S. Malka, Total Knee Replacement, 3 pages.
Webpage, Synvasive® Technology, Inc., Design Available for Your Knee, 2 pages.
Webpage, Orthopaedic Connection, Total Joint Replacement, 2000, 4 pages.
Webpage, American Association of Orthopaedic Surgeons, Total Knee Replace, Jul. 2001, 11 pages.

* cited by examiner

METHOD FOR KNEE-JOINT SURGERY

CROSS REFERENCE TO RELATED APPLICATIONS

This application is a continuation-in-part of application Ser. No. 10/623,179; filed Jul. 18, 2003, which is hereby incorporated by reference in its entirety, which claims priority of U.S. Provisional Application No. 60/396,850, filed Jul. 18, 2002, the content of which is hereby incorporated by reference in its entirety.

This application is also a continuation-in-part of application Ser. No. 10/728,202 filed on Dec. 4, 2003, now U.S. Pat. No. 7,264,589 which is hereby incorporated by reference in its entirety, which is a continuation of application Ser. No. 10/077,693, filed Feb. 15, 2002, now U.S. Pat. No. 6,659,944 which is incorporated by reference in its entirety, which is a continuation of application Ser. No. 09/990,420 filed on Nov. 21, 2001, which is incorporated by reference in its entirety, and resulting in U.S. Pat. No. 6,368,271.

BACKGROUND OF THE INVENTION

The present invention relates to a method for performing knee-joint replacement surgery. More particularly, the present invention relates to a method for performing a knee-joint replacement surgery with the aid of retractors retained by a support apparatus secured to a surgical table.

The knee-joint is the largest and the most complex joint in the body. The knee joint is the articulation of three bones consisting of the lower femur, the upper tibia and the upper tibia and the patella which is commonly known as the knee-cap. Large ligaments attach the femur to the tibia to provide stability to the knee joint.

The joint surfaces of the femur, the tibia and the patella are covered with articular cartilage that cushions the bones. Along with the articular cartilage the femur and the tibia are separated by lateral and medial menisci which are pads of cartilage that act as shock absorbers between the two bones. All remaining surfaces of the tibia, femur and patella that make up the knee joint are covered by a synovial membrane that releases synovial fluid that lubricates the knee and reduces friction in a healthy knee to nearly zero.

When the knee-joint functions properly, the upper end of the tibia and the lower end of the femur glide with respect to each other and allow the knee to bend. The synovial fluid coated cartilage, including the menisci, separates the lower end of the femur and upper end of the tibia and provides cushioning between the tibia and femur similar to a shock absorber and smoothly articulate with nearly no friction.

The most common cause of chronic knee pain is arthritis of which osteoarthritis, rheumatoid arthritis and post traumatic arthritis are the most common forms. Osteoarthritis typically occurs after the age of 50 and is caused by the softening and wearing away of the cartilage including the menisci. As the cartilage is worn away, the tibia and femur rub against each other which causes pain and stiffness.

The second type of arthritis is rheumatoid arthritis which causes the synovial membrane to become thickened and inflamed, producing excessive amounts of synovial fluid which over-fills the joint space. The chronic inflammation can damage the cartilage and eventually cause cartilage loss, pain and stiffness.

The third type of arthritis is post traumatic arthritis which follows a serious knee injury. A knee fracture or severe tear of the knee ligaments may damage the cartilage over time. The damage to the cartilage causes pain and stiffness in the knee joint.

The arthritis in the knee can become painful to the point of extremely limiting the person's mobility. When medications such as analgesics cannot eliminate or make the pain manageable, an increasingly popular option is to have a total knee replacement operation where the damaged knee joint is replaced with an artificial knee-joint called a prosthesis.

The current procedure for performing a total knee replacement surgery is very taxing on the surgical personnel. An incision is made from the top of the knee exposing the patella. A retractor is disposed into the incision and to one side of the patella. The surgical personnel manually retract the patella to one side and use additional retractors to manually retract the flesh to expose the femur and tibia.

With the femur and tibia exposed, the joint is separated to gain access to either the end of the femur or the tibia typically by adjusting the position of the tibia which requires additional personnel. The ends of the femur and tibia are precisely cut and inserts are attached to each end of the bones. Typically, a metal piece made of highly polished stainless steel or titanium is inserted into the femur and an insert made of a durable, non-wearing plastic, typically polyethylene, is inserted into the tibia. The interface of the metal and the plastic provides a smooth moving joint that does not require lubrication.

One way to reduce the physical nature of the operation and the number of personnel required to perform the procedure is to use retractors secured to a support that is secured to a surgical table to retract the flesh to expose the surgical site. U.S. Pat. No. 6,315,718 discloses a table mounted retractor system for a method of hip retraction. The table mounted retractor system discloses using a table mounted support apparatus to support both flesh retracting retractors to expose the hip joint and bone retracting retractors to dislocate and displace the femoral ball from the acetabulum.

SUMMARY OF THE INVENTION

The present invention includes a method of performing knee-joint surgery. With the patient lying on a surgical table, the tibia and the femur are positioned to place the knee-joint in a bent position. An incision is made to expose the knee-joint. A retractor support is mounted onto the surgical table. Skin and flesh layers proximate the knee-joint are retracted utilizing a retractor. The retractor IS ached to the retractor support exposing the knee-joint

DETAILED DESCRIPTION OF THE PREFERRED EMBODIMENTS

The present invention includes a method for performing knee-joint replacement surgery that utilizes surgical retractors that are secured to a retractor support apparatus that is mounted to a surgical table. Preferably, the knee-joint replacement surgery is performed in a manner that does not require repositioning of the surgical retractors within the incision or re-securing the surgical retractors to the support apparatus during the surgical procedure.

Figure 1:
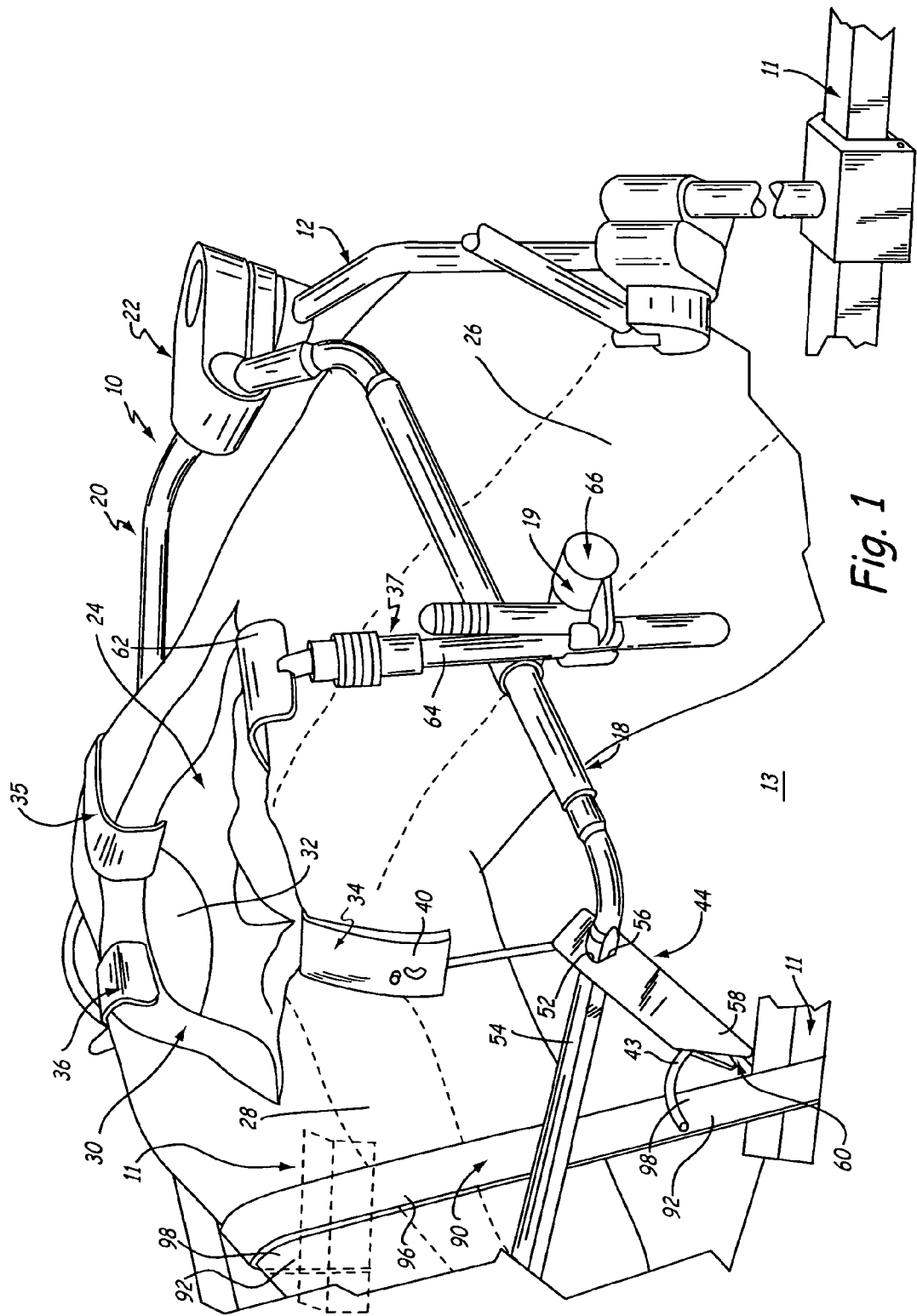
FIG. 1 is a perspective view of the apparatus used in the surgical procedure of the present invention.

The apparatus used in the knee-joint replacement surgery of the present invention is generally indicated at 10 in FIG. 1. The apparatus 10 includes a retractor support apparatus 12 that is rigidly mounted to a rail 11 of a surgical table 13 in a manner that is well known in the art and is described in U.S. Pat. Nos. 4,617,916, 4,718,151, 4,949,707, 5,400,772, 5,741, 210, 6,042,541, 6,264,396 and 6,315,718 all of which are herein incorporated by reference. From the mount to the surgical table 13, the retractor support apparatus 12 includes first and second support arms 18 and 20 that extend over the surgical table. The support arms 18 and 20 are independently adjustable into an infinite number of selected positions through use of a clamping mechanism 22 which is described in U.S. Pat. Nos. 5,899,627 and 6,264,396, which are herein incorporated by reference. The support arms 18 and 20 extend in a generally lateral or horizontal direction on opposite sides of a knee-joint 24. The clamp 22 secures the adjustable support arms 18 and 20 in selected angular positions with respect to the knee-joint 24.

The knee-joint 24 is preferably placed in and supported in a bent position as is typically done in knee-joint replacement surgery. The bent position is approximately a 90° angle between the femur 26 and the tibia 28. The support arms 18 and 20 are disposed on both sides and below the knee-joint 24.

An incision 30 is made on top of the knee to gain access to the joint 24. The incision is made directly over the patella 32 or on occasion to the left or right of the patella 32 depending on the surgeon's preference, and/or the type of surgical procedure to be performed. Once the incision 30 is made, a plurality of retractors 34, 35, 36 and 37 are positioned in selected positions to manually retract skin and flesh layers to expose the knee-joint 24. Once in the selected positions, the retractors 34, 35, 36 and 37 are supported by and retained to the adjustable support arms 18 and 20 that are components of the retractor support apparatus 12 that is mounted to the rail 11 of the surgical table 13.

One skilled in the art will recognize that any knee-joint replacement surgical procedure, including a total knee-joint replacement and/or a partial knee-joint replacement, can be performed using the retractors 34, 35, 36 and 37 that are supported and retained by the table mounted retractor support apparatus 12. By total knee-joint replacement is meant a surgical procedure where all of the contacting surfaces of lower end of the femur and the upper end of the tibia and optionally, the patella are replaced. By partial knee-joint replacement is meant a surgical procedure where the worn or damaged contacting surfaces of the lower end of the femur and the upper end of the tibia are replaced while the healthy portion of the knee-joint remains intact.

Figure 3:
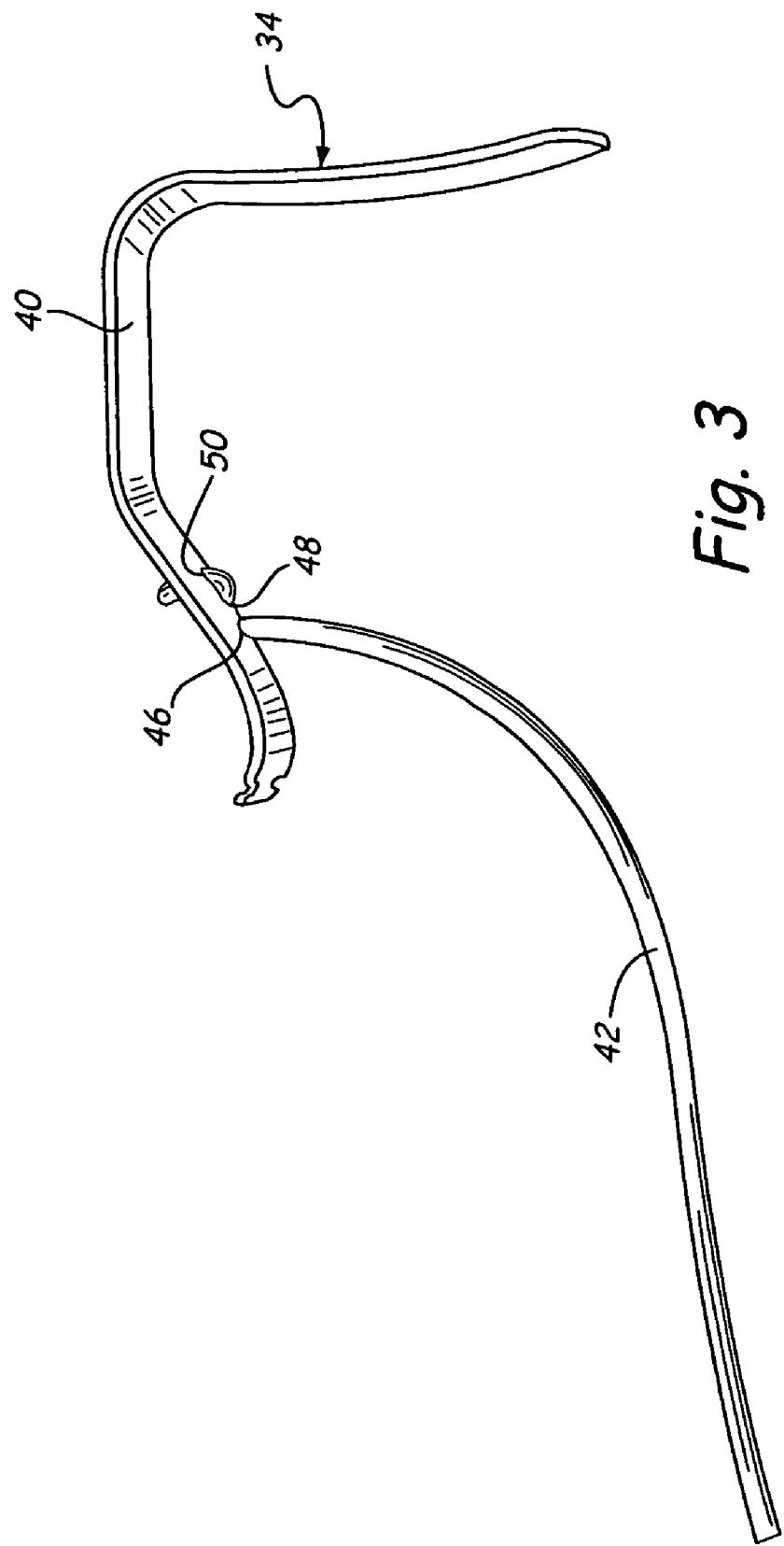
FIG. 3 is a side view of a surgical retractor for use in the method of the present invention.

Since both surgical retractors 34 and 36 are of the same construction only retractor 34 will be described in detail. As best illustrated in FIG. 3, the surgical retractor 34 includes a retractor blade 40 attached to a flexible connector 42 such as plastic cord. The flexible connector 42 is connected to the support arm 18 by an attaching device 44.

It should be understood that although a cord is illustrated other types of flexible connectors may be used in the method of the present invention. What is important is that the retractor starting from its attachment to either support arm 18 or 20 to the skin and flesh layers not be rigid. The procedure of the present invention permits the tibia 28 or femur 26 to be moved in relation to each other without necessitating repositioning of the retractor blade, repositioning the attachment of the retractor to the retractor support or moving (adjusting) the retractor support. The flexible connector also needs to have sufficient integrity and strength to retain the retractor blade in a flesh retracted position. Although the flexible connector as shown extends from the retractor blade 40 to the attaching device 44, the flexible connector does not necessarily have to extend from the blade 40 to the device 44. For example, only a portion of the flexible connector could be flexible while the remainder could be rigid as long as sufficient flexibility exists between the retractor blade 40 and the support arm 18 or 20 to be able to reposition the tibia 28 in relation to the femur 26. For example, the flexible connector 42 may also be elastic or be made of resilient material as long as the connector is flexible. By flexible is meant that the surgeon may adjust the position of the knee-joint during surgery without having to reposition the retractor blade, reattach the retractor to the retractor support or adjust the position of the retractor support.

It is preferred that at least one of the retractors includes a flexible connector. As illustrated in FIG. 1, standard rigid retractors 37 without a flexible connector can also be used in the surgical procedure of the present invention. In other words, not all of the retractors used in the method of the present invention need to have a flexible connector. Surgical retractors which are rigid are well known in the art and are secured to the support arm 18 by a clamping mechanism 19 that is also well known. A rigid retractor 37 can be used as long as the surgeon can adjust the position of the knee-joint during surgery without having to reposition the retractor blade, reattach the retractor to the retractor support or adjust the position of the retractor support.

The flexible connector 42 is typically made of a polymeric material in the form of a solid cord. However, the connector 42 may be of any construction such as woven, braided, non-woven material or flexible metal. The flexible connector 42 is frictionally attached to the retractor blade 40 by extending through a series of holes 46, 48 and 50 in a serpentine fashion.

Knee-joint replacement surgery due to the unique positioning of the knee-joint and its relatively light weight has posed a problem in terms of retraction of the skin and flesh. Table mounted retractors have been used for surgery on various areas of the torso. However, the torso lies flat on the surgical table and is of sufficient weight that rigid surgical retractors pulling up from an elevated position do not move the torso. However, a knee-joint must be positioned in a bent and elevated position. The knee-joint also does not have the weight of a torso. Consequently retraction of the knee-joint has required significant manual assistance for proper retraction. Utilizing the procedure of the present invention by securing retractors to a table mounted support eliminates the need for additional surgery personnel to manually assist for proper retraction in holding the incision open.

As best illustrated in FIG. 1, the retractor blade 40 is positioned to engage and retract flesh along the incision 30. The flexible connector 42 is then manually pulled to retract the skin and flesh layers, opening the incision and exposing the knee-joint. With the skin and flesh layers retracted to expose the knee-joint, the retractor blade 40 is secured in a selected position by engaging the flexible connector 42 with the attaching device 44. Since the support arms 18 and 20 are positioned below the knee-joint, the force against the retracted skin and flesh is disposed along a downward slope from the point of retraction to either the support 18 or 20.

The attaching device 44 is secured to the support arm 18 through aperture 52 through which the support arm 18 extends. To prevent the attaching device from rotating about the support arm 18, the support arm 18 includes a flat section 54 that cooperates with or acts against a flat or straight section 56 of the aperture 52. The support arm 20 also has a like flat section (not shown) for the same purpose. It should be understood by those skilled in the art that other methods of preventing rotation of the attaching device 44 about the arm 18 are included within the scope of the present invention. Such other methods of retaining the attaching device 44 may include clamps, set screws, pins and the like.

The attaching device 44 extends in a direction generally away from the incision 30 and has a distal end 58 that includes a V-shaped notch 60. When the flexible connector 42 is pulled back, a free end 43 of the connector is inserted between opposing sides of the V-shaped notch 60 for engagement. The V-shaped notch 60 pinches the flexible connector 42, thereby holding or retaining the flexible connector 42 in a pinched or frictional engagement.

Figure 2:
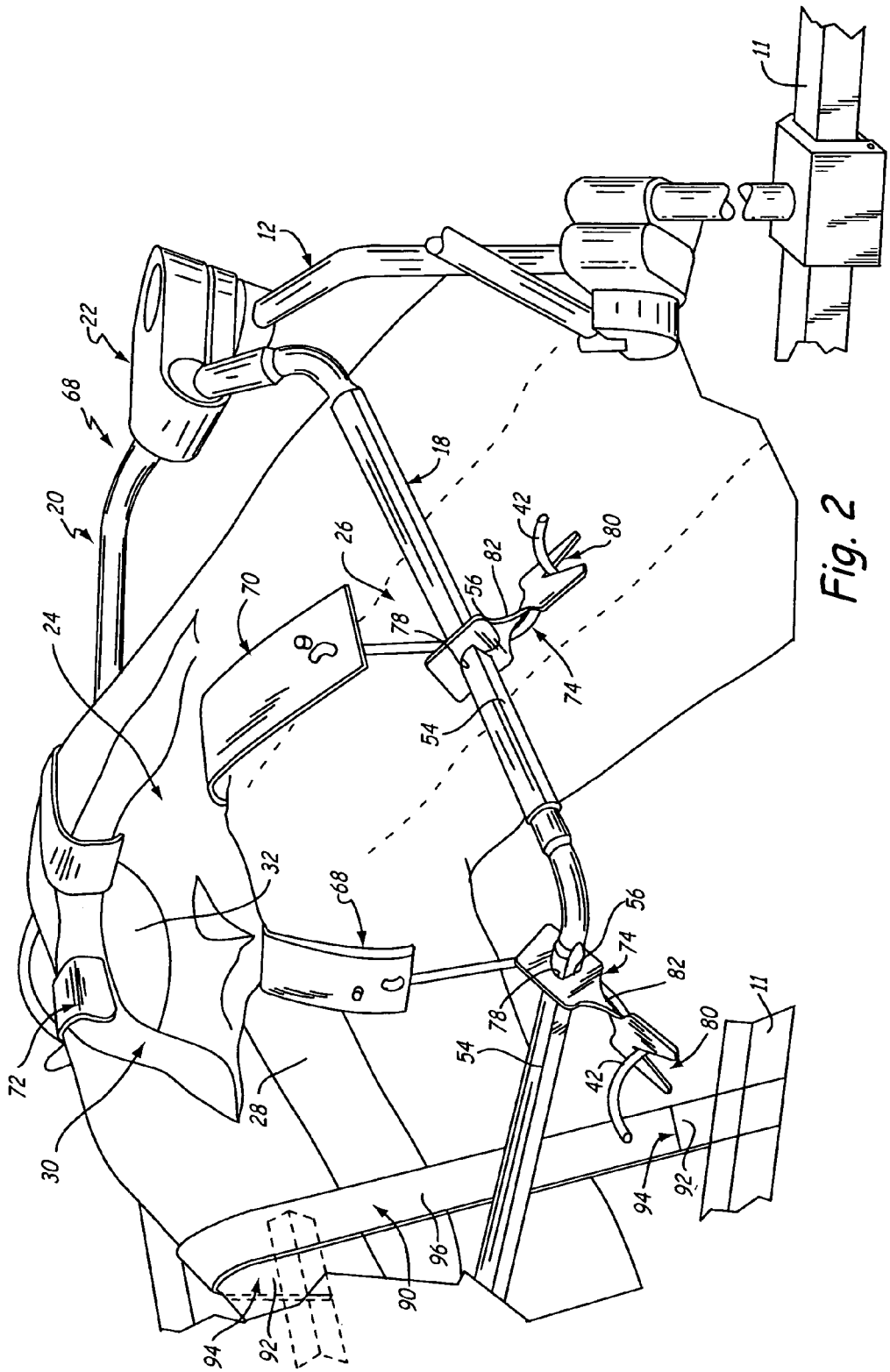
FIG. 2 is a perspective view of an alternative apparatus used in the surgical procedure of the present invention.

The surgical procedure of the present invention can be performed entirely using the retractor with flexible connectors of the present invention as illustrated in FIG. 2, wherein like reference characters will be used to indicate like elements of FIG. 1. The apparatus generally indicated at 68 includes retractors 68, 70, 72 and 73, all which have flexible connectors 42. All are mounted to either one of the support arms 18 and 20 which in turn is mounted to the rail 11 of the surgical table 13.

The flexible connector 42 of the surgical retractor 68, 70, 72 and 73 is attached to the support arms 18 and 20 by an attaching device 74 that has a different configuration than the attaching device 44 illustrated in FIG. 1. However, the attaching device 74 is secured to the support arms 18 and 20 in a similar fashion, and that is by an aperture 76 having a flat section 78 that cooperates or acts against the flat section 54 of the support arm 18. Similarly, the flexible connector 42 is engaged in a V-shaped notch 80 similar to the V-shaped notch 60 of the attaching device 44. The primary difference between the attaching device 74 and the attaching device 44 illustrated in FIG. 1 is that the attaching device 74 is made of flat sheet metal wherein the mid-section 82 of the device 74 is twisted approximately 90° to provide rigidity to the attaching device. Rigidity is provided to the attaching device 44 by virtue of its arcuate cross-section.

Ends 92 of a lower leg hold down device 90 are attached to the side rails 11 of the surgical table 13, respectively. The hold down device 90 includes a flexible strap 96 having the ends 92 attached to the side rails 11 with securing devices 96. The flexible strap 96 is attached to the side rails 11 with securing devices 98 that slidably attach the strap 96 to the side rails 11 at a position below the point at which the strap 96 engages the lower leg so that a force is applied to the lower leg to retain the lower leg in position. Suitable securing devices 98 include a velcro fastener, a snap, a button, a zipper, a buckle, a sewn loop or any other fastening device that secures the ends 92 of the flexible strap 96 to the rails 11. Holding the lower leg down in position eliminates the need for manual retention of the lower leg during surgery or the use of other additional devices that may be secured to the working surface of the surgical table.

With the knee-joint exposed by retracting skin and flesh layers with retractors 34, 35, 36 and 37 supported and retained in the retracting position by the table mounted surgical support 12, one of a number of surgical procedures can be performed to the knee-joint. In a total knee-joint replacement surgery, the patella 32 is either removed or moved aside to gain access to the ends of the femur 28 and the tibia 26. Due to the flexible connector 42 of the retractors 34, 36, the knee-joint can be repositioned without having to adjust the position of the support arm 18 or 20 or readjusting the retractor blade or reattaching the retractor blade to either support arm or both, 18 and 20.

Since the knee-joint 24 is in a bent position, the end of the femur 28 is accessible to the surgeon through the incision 30. The end of the femur 28 is then cut, and prepared to accept a prosthetic insert (not shown) made of metal such as stainless steel or titanium as is standard in knee-joint replacement.

The end of the femur 28 can be cut to prepare a surface for an insert (not shown) to be secured to the femur 28. Alternatively, the front, the back and the end of the femur can be cut to prepare surfaces for the insert (not shown) to be attached to the femur 28. The insert is preferably made of a highly polished metal such as stainless steel titanium. The insert can be shaped to conform to the three cut surfaces of the femur and cemented into place. The insert may also include a single shaft or a plurality of pegs that are inserted to cooperating apertures that are reamed into the femur and cemented into place. Alternatively, the insert may be positioned onto the femur such that a mesh-like surface engages the femur and allows the bone to grow onto the insert to secure the insert to the femur 28.

After the end of the femur 28 has been prepared to accept the prosthetic insert (not shown), the tibia 26 is also prepared to accept a second prosthetic insert (not shown). To prepare the tibia 26 to accept the second prosthetic insert, the tibia 26 must be pushed away from the femur 28 and lifted to gain access to the end of the tibia 26. Since the retractors of the present invention have flexible connectors 42, the tibia 26 may be moved with respect to the femur 28 without the need to reposition retractor blades or reattach the retractors to the support arms 18 or 20 or adjust the support arms 18 or 20.

Having gained access to the tibia 26, the surgeon cuts the end of the tibia 26 and secures the second prosthetic insert (not shown) hereto. The insert (not shown) for the tibia can be made of polymer, such as polyethylene, which interacts with the polished metal fist prosthetic insert attached to the femur 28. Alternatively, the insert may include two components, a highly polished metal component (not shown) secured to the tibia 26 and a polymer component (not shown) that is secured to the metal component and interacts with the first femoral insert. The metal component may include a shaft or a number of pegs that engage complimentary indentions that are reamed into the tibia 26. Alternatively, the metallic portion insert may include a mesh-like surface that is positioned proximate the tibia where the bone grows onto the insert to secure the metallic portion of the insert to the tibia. Although either insert is within the scope of the present invention, the two component insert provides an advantage of replacing only the polymeric portion of the insert without having to perform surgery on the tibia in the event the polymeric portion of the insert wears and causes the patient discomfort. With the prosthetic insert secured to the tibia, the tibia is then maneuvered to engage the prosthetic insert on the femur.

The highly polished insert attached to the femur 28 engages the high density polymer insert attached to the tibia 26 such that the interaction of the inserts is almost frictionless and resembling the function of a healthy knee-joint 24. One skilled in the art will recognize that in a total knee-joint replacement surgery all of the cartilage and synovial membrane attached to the tibia and the femur are removed, thereby requiring the nearly frictionless interaction between the inserts attached to the femur and the tibia.

Although the total knee-joint replacement surgery described first prepares the femur for the insert and then prepares the tibia for the insert, it is within the scope of the present invention to first prepare the tibia followed by the femur for accepting prosthetic inserts. Additionally, it is within the scope of the present invention to replace the damaged end of either the femur or the tibia with an insert while leaving the undamaged end of the other bone intact.

Once the two prosthetic inserts are engaged, the surgical procedure may include attaching a prosthetic insert (not shown) to a back side of the patella 32 depending upon the damage or wear to the patella 32. If the patella 32 requires an insert, the insert is secured to the patella 32 with cement. The insert, also referred to as a button, may also include pegs that are inserted into indentions reamed into the back of the patella 32 to better secure the insert to the patella 32. With the insert secured to the patella 32, the patella 32 is repositioned into the knee-joint 24 such that the button engages a groove in the front side of the insert attached to the femur 28 such that the interaction between the button and the femoral insert resemble the interaction between a healthy patella 32 and a healthy end of the femur 28. Alternatively, if the patella 32 is not damaged, the patella 32 may be repositioned into the knee-joint 24.

Once the inserts have been secured to the femur 28, the tibia 26 and optionally the patella 32, the retractors 34, 35, 36 and 37 are removed from the incision 30 and the incision 30 is sutured closed. A drain (not shown) may be positioned within the knee-joint 24 to remove excess blood and fluids that may accumulate in the knee-joint caused by the trauma from the total knee-joint replacement surgery. Once the knee-joint 24 stops draining, the drain is removed and the incision 38 is completely closed.

Alternatively, a partial knee-joint replacement surgery can be performed with a portion of the knee-joint 24 exposed by retracting skin and flesh layers with retractors 34, 35, 36 and 37 supported and retained in the retracting position by the table mounted surgical support. A partial knee-joint replacement replaces only the damaged portion of the knee-joint such as a medial side or a lateral side of the knee-joint. The same type of procedure is used as in a total knee-joint replacement surgery where inserts replace the damaged ends of the bones. However, the incision is considerably smaller, resulting in less blood loss, trauma and a shorter recovery period.

The incision is made on the knee-joint 24 on the side of the partial knee-joint replacement surgery. The incision 30 is retracted as previously described with retractors supported and attached to a table mounted retractor support apparatus 12. Only the damaged portion of the femur 20 is cut to provide a surface for securing the highly polished metal femoral insert (not shown). The damaged portion of the tibia 26 is also cut to remove the damaged portion and provide a securing surface for the insert (not shown) to be secured to the tibia 26. The fibial insert may be made of solid high density polymer such as polyethylene or may include a metallic portion that is secured to the tibia and a polymeric portion that is secured to the metallic portion. With the two inserts secured to the femur 28 and the tibia 26, the inserts are positioned proximate each other such that the engagement of the inserts resembles the movement of the healthy side of the knee-joint 24.

With the inserts secured to the femur 28 and the tibia 26, the retractors 34, 35, 36 and 37 are removed from the incision 30. The incision 30 is then sutured shut.

Although the present invention has been described with reference to preferred embodiments, workers skilled in the art will recognize that changes may be made in form and detail without departing from the spirit and scope of the invention.

What is claimed is:

1. A method of performing a knee-joint surgery involving a tibia and femur on a surgical table, the method comprising:
    mounting a retractor support to the surgical table wherein the retractor support comprises first and second support arms the first and second support arms defining an opening;
    positioning the tibia and the femur such that the knee-joint is disposed in a bent position through the opening;
    wherein the step of positioning includes placing the first and second support arms over the surgical table, on opposite sides of a portion of the upper leg or thigh, below the knee joint, and about a portion of the lower leg or shin;
    incising skin and flesh layers proximate the knee-joint;
    retracting the skin and flesh layers proximate the knee-joint with a retractor; and
    attaching the retractor to either the first support arm or the second support arm.

2. The method of claim 1 wherein the retractor support is mounted to a rail of the surgical table.

3. The method of claim 1 wherein the retractor is attached to the retractor support with a flexible cord.

4. The method of claim 3 wherein the flexible cord is attached to the retractor support by engaging a member that is rigidly attached to the retractor support, the member having a groove wherein the cord engages the groove.

5. The method of claim 1 wherein the retractor is attached to the retractor support in a manner so that the knee joint may be moved during surgery without repositioning the retractor.

6. The method of claim 1 and wherein the knee-joint surgery comprises a knee-joint replacement surgery wherein a femoral insert is secured to the femur and a tibial insert is secured to the tibia.

7. The method of claim 6 and further comprising securing an insert to the patella that engages the femoral insert.

8. The method of claim 1 and wherein the knee-joint surgery comprises a partial knee-joint replacement surgery wherein damaged portions of the tibia and the femur are replaced with inserts that are secured to both the tibia and the femur and wherein cartilage remains between the tibia and the femur.

* * * * *